(12) United States Patent
Houjou et al.

(10) Patent No.: US 8,379,305 B2
(45) Date of Patent: Feb. 19, 2013

(54) OBSERVATION UNIT

(75) Inventors: Mikio Houjou, Higashiosaka (JP); Seiji Murakami, Moriguchi (JP); Yasuhiro Asai, Kasai (JP); Yoshitaro Yamanaka, Kyoto (JP); Takahiro Inoue, Hirakata (JP)

(73) Assignee: Sanyo Electric Co., Ltd., Moriguchi-shi (JP)

( * ) Notice: Subject to any disclaimer, the term of this patent is extended or adjusted under 35 U.S.C. 154(b) by 578 days.

(21) Appl. No.: 12/629,288

(22) Filed: Dec. 2, 2009

(65) Prior Publication Data
US 2010/0157423 A1 Jun. 24, 2010

(30) Foreign Application Priority Data
Dec. 19, 2008 (JP) .................................. 2008-324661

(51) Int. Cl.
*G02B 21/26* (2006.01)
(52) U.S. Cl. ........................................................ 359/395
(58) Field of Classification Search .................. 359/391, 359/395
See application file for complete search history.

(56) References Cited

U.S. PATENT DOCUMENTS

| 6,233,093 | B1 * | 5/2001 | Arnold et al. ................. 359/395 |
| 7,233,438 | B2 * | 6/2007 | Tokunaga et al. ............. 359/395 |
| 7,502,165 | B2 * | 3/2009 | Wehner et al. ................ 359/395 |
| 8,110,394 | B2 * | 2/2012 | Hasegawa et al. ......... 435/288.7 |
| 2005/0282268 | A1 | 12/2005 | Kagayama |
| 2010/0208053 | A1 * | 8/2010 | Hasegawa et al. ............. 348/79 |

FOREIGN PATENT DOCUMENTS

| DE | 10 2005 033 927 A1 | 6/2007 |
| EP | 1 677 136 A1 | 7/2006 |
| EP | 1 997 876 A1 | 12/2008 |
| JP | 2007-209258 A | 8/2007 |

\* cited by examiner

*Primary Examiner* — Frank Font
(74) *Attorney, Agent, or Firm* — Marvin A. Motsenbocker; Mots Law, PLLC

(57) ABSTRACT

The observation unit according to the present invention comprises an observation device observing a sample, a placing table on which the sample is placed, a drive device moving the placing table to an observation position where the sample is observed by the observation device, and a casing sealing a first space extending in a vertical direction. The first space and the placing table are arranged so as to be displaced from each other in a horizontal direction, and the drive device is arranged in the first space.

5 Claims, 16 Drawing Sheets

OBSERVATION UNIT

The application Number 2008-324661, upon which this patent application is based, is hereby incorporated by reference.

BACKGROUND OF THE INVENTION

1. Field of the Invention

The present invention relates to observation units used in an incubator, an isolator or the like. The incubator controls a culture environment in which cells are cultured, and the isolator is a device which includes a sterile space for biological or chemical work.

2. Description of Related Art

Conventionally, an incubator has been used as a device for culturing a sample such as a cell. However, in a conventional incubator, it is necessary to take out the sample from the incubator in order to observe condition of the sample under culture. However, the sample such as a cell is sensitive to temperature change, and therefore, when taken out from the incubator, the sample can be affected such that the cell is killed, for example.

In view of above problem, it has been proposed to provide the incubator with an observation device so that the condition of the sample can be observed with the sample being in the incubator. In this incubator, a projecting part is formed on an outer surface of a casing forming the incubator. In the projecting part, defined is a space in which the sample is to be placed for observation. The space is in communication with a space in the incubator. Also, the projecting part is provided with a window on top and bottom thereof each. Light can thereby pass through the space in the projecting part via the two windows on the top and bottom of the projecting part. On the outer surface of the casing, a microscope unit is arranged so as to sandwich the projecting part from upper and lower sides thereof.

With the incubator described above, it is possible to observe the sample under the environment in the incubator by moving the sample from the space in the incubator to the space in the projecting part. Therefore, it is not necessary to take out the sample from the incubator for observation of the sample.

However, the incubator described above is provided with the observation device (the microscope unit) on the outside thereof, resulting in an increase in size of the incubator. Also, the observation device is specific to the incubator described above, and therefore, it is difficult to apply the observation device to other incubators, resulting in low applicability.

For example, arrangement of the observation device in the incubator can be thought. However, if the conventional observation device is provided in the incubator without change, the observation device will be exposed to the environment in the incubator, and problems can be caused in an optical system or an imaging system of the observation device by moisture or the like.

Further, in the case of arranging the observation device in the incubator, the observation device needs to be automated and provided with a drive motor or the like for focusing. However, when being operated, the drive motor generates a large amount of heat, and the heat can be conducted to the sample and affect the sample.

SUMMARY OF THE INVENTION

In view of above described problem, an object of the present invention is to provide an observation unit which can be used in a storage such as an incubator, an isolator or the like without affecting a sample.

A first observation unit according to the present invention comprises an observation device observing a sample, a placing table on which the sample is placed, a drive device moving the placing table to an observation position where the sample is observed by the observation device, and a casing sealing a first space extending in a vertical direction. The first space and the placing table are arranged so as to be displaced from each other in a horizontal direction, and the drive device is arranged in the first space.

With the first observation unit, heat generated in the drive device is conducted to the ambient air to rise together with the air, and therefore, the heat of the drive device is hardly conducted to the placing table arranged at a position displaced from the drive device in the horizontal direction. Accordingly, the heat is hardly conducted to the sample placed on the placing table as well, resulting in inhibition of temperature increase of the sample. Therefore, it is possible to observe the sample without subjecting the sample to influence of heat such that cultivation of the sample is prevented, the sample is killed, or the like.

Further, the first observation unit can be easily made smaller, and therefore, it is possible to take the observation unit into or from the storage such as an incubator or the like, resulting in an increase in applicability.

A second observation unit according to the present invention is the first observation unit described above, wherein the observation device comprises an optical system and an imaging system, the imaging system is arranged in the first space while the optical system is arranged in a second space arranged below the placing table and sealed by the casing, and a shielding member preventing heat transfer from the first space to the placing table and the second space is interposed between the first space and the placing table and between the first space and the second space. Also, a light transmission part transmitting light from the observation position downward to the optical system of the observation device is formed on an upper surface wall of the casing. The upper surface wall forms a top part of the second space.

With the second observation unit, the shielding member is interposed between the first space and the placing table and between the first space and the second space, and therefore, the heat generated in the drive device and the imaging system of the observation device in the first space is prevented from being transferred to the placing table and the second space by the shielding member. Therefore, even in the case where heat is generated in the drive device and the imaging system of the observation device, the temperature of the sample scarcely increases. Accordingly, it is possible to observe the sample without subjecting the sample to the influence of heat.

Moreover, the drive device and the observation device are arranged in the spaces (the first space and second space) sealed by the casing, and therefore, even in the case where the observation unit is arranged in the storage, the drive device and the observation device are not exposed to an environment in the storage. Therefore, problems of the drive device and the observation device caused by moisture or the like hardly occur.

Although the observation device is arranged in a sealed space, since the casing is provided with the light transmission part, the observation of the sample by the observation device is not prevented by the casing.

A third observation unit according to the present invention is the second observation unit described above, wherein a heat insulating layer is formed between the top surface wall of the casing forming the top part of the second space and the placing table.

With the third observation unit, even in the case where the heat generated in the drive device and the imaging system of the observation device is conducted to the casing and transferred to the top surface wall forming the top part of the second space, since the heat insulating layer is formed between the top surface wall and the placing table, the heat is hardly conducted to the placing table, resulting in preventing the temperature increase of the sample. Accordingly, it is possible to observe the sample without subjecting the sample to the influence of heat.

A fourth observation unit according to the present invention is the third observation unit described above, wherein at least a part of the heat insulating layer is formed by a heat insulating member, and the light transmission part penetrates the heat insulating member to be exposed on a surface of the heat insulating member.

A fifth observation unit according to the present invention is any one of the second to fourth observation units described above, wherein the placing table is capable of reciprocating between the observation position and a separated position which is separated from a position above the second space, and reciprocating movement of the placing table is executed by the drive device.

With the fifth observation unit, it is possible to inhibit heat transfer from a heat source such as the drive device, the imaging system of the observation device or the like to the sample by moving the placing table to the separated position at the time other than observation.

A sixth observation unit according to the present invention is any one of the first to fifth observation units described above, wherein drive force of the drive device is transmitted to the placing table by a transmission member, the placing table can be attached to and detached from the transmission member, the transmission member is provided with a detection part while the placing table is provided with a to-be-detected part which is to be detected by the detection part, and the to-be-detected part is arranged so that a center of the sample placed on the placing table matches a predetermined position when the to-be-detected part is detected by the detection part.

With the sixth observation unit, even in the case where the placing table is replaced with one having a different shape, the center of the sample can be easily matched to the predetermined position.

DETAILED DESCRIPTION OF THE PREFERRED EMBODIMENT

A preferred embodiment of the present invention is described in detail below with reference to the drawings.

1. Usage Configuration of Observation Unit

Figure 1:
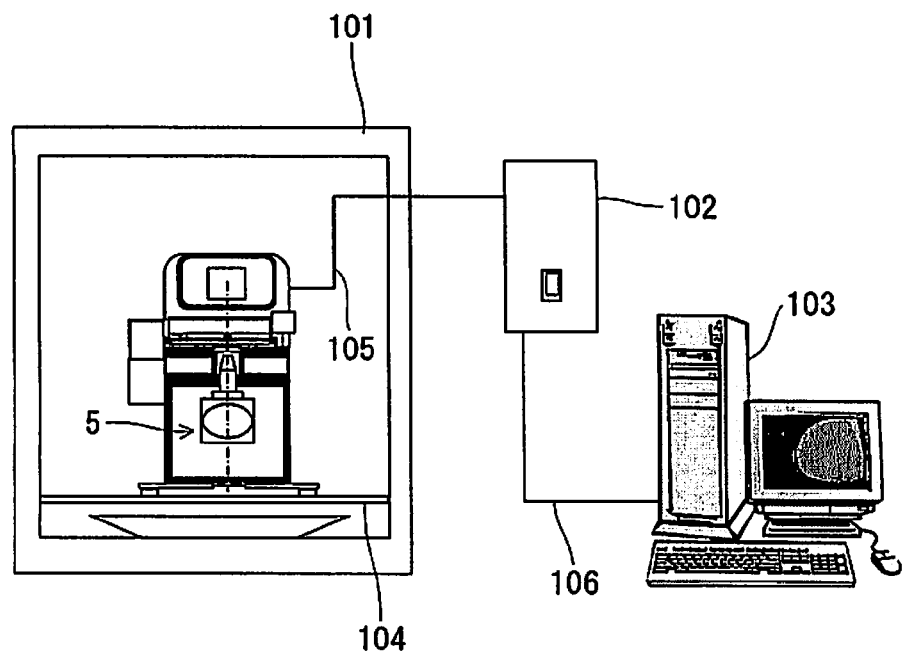
FIG. 1 is a view showing a usage configuration of an observation unit according to an embodiment of the present invention.

FIG. 1 is a view showing a usage configuration of an observation unit according to the embodiment of the present invention. As shown in FIG. 1, the observation unit can be taken into and from a storage 101 for culturing or storing a sample such as a cell or the like. The storage 101 includes an incubator, an isolator and the like. The storage 101 is provided therein with a shelf 104, and the observation unit is arranged on the shelf 104 to be used.

Although the storage 101 shown in FIG. 1 is merely provided with one shelf 104, the storage 101 can be provided therein with a plurality of shelves so that a plurality of fluid vessels containing the sample can be stored.

The observation unit is connected to a control device 102 installed outside the storage 101 via a cable 105. The control device 102 controls the observation unit and is provided therein with a driver, a controller and the like for driving the observation unit.

The control device 102 is connected to a personal computer 103 installed outside the storage 101 via a cable 106. Therefore, it is possible that the personal computer 103 gives an instruction to the control device 102 to control the observation unit, an observation image is obtained and stored, and the like.

2. Structure of Observation Unit

Figure 2:
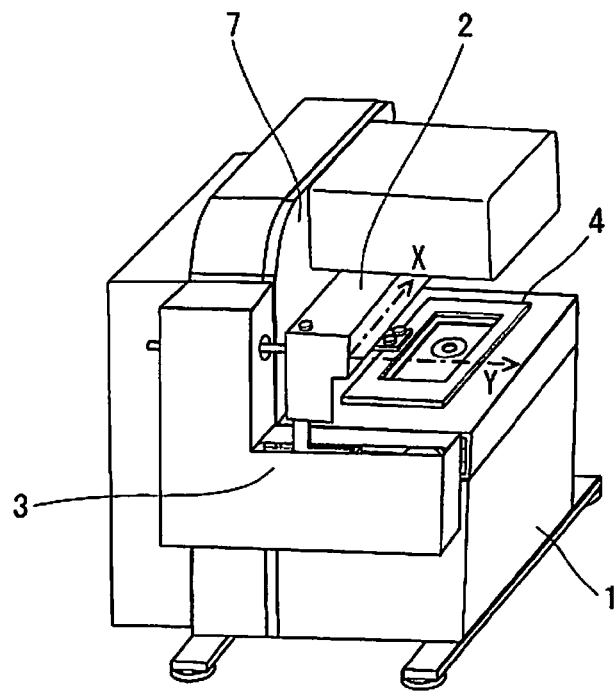
FIG. 2 is a perspective view showing an appearance of the observation unit.
Figure 3:
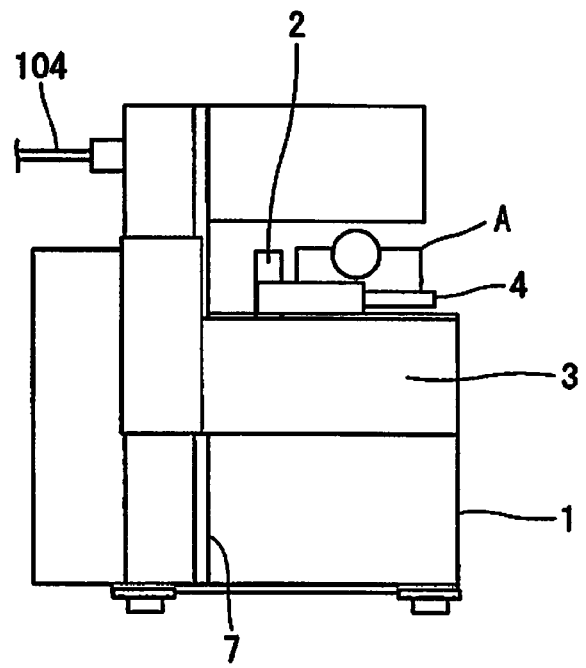
FIG. 3 is a side view of the observation unit.
Figure 4:
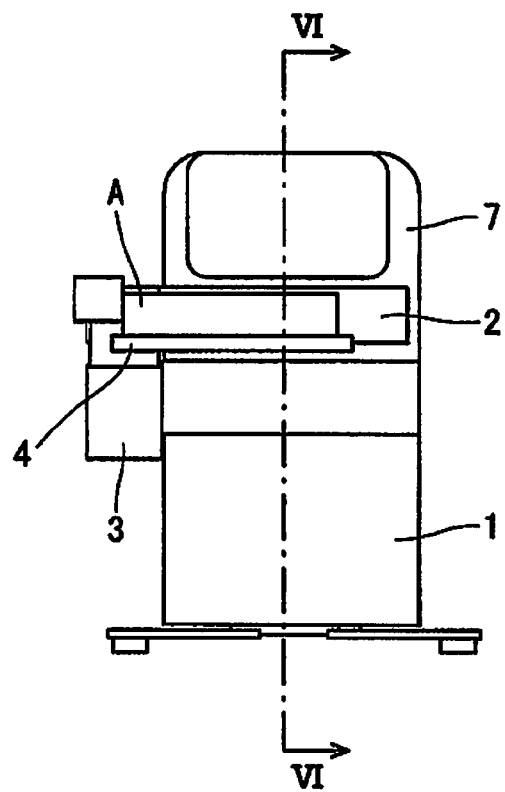
FIG. 4 is a front view of the observation unit.
Figure 5:
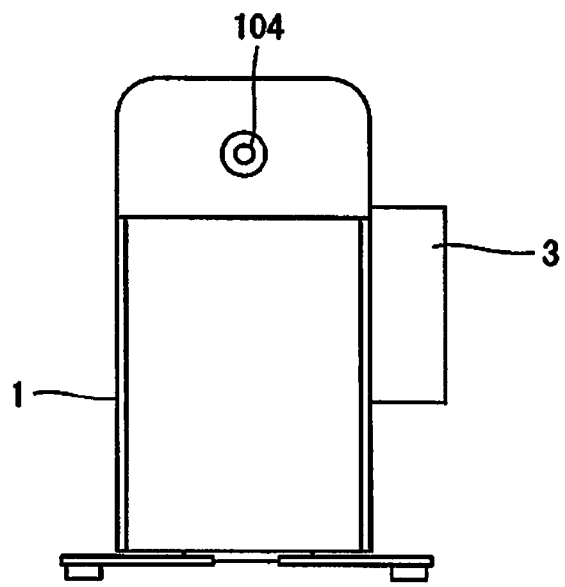
FIG. 5 is a rear view of the observation unit.
Figure 6:
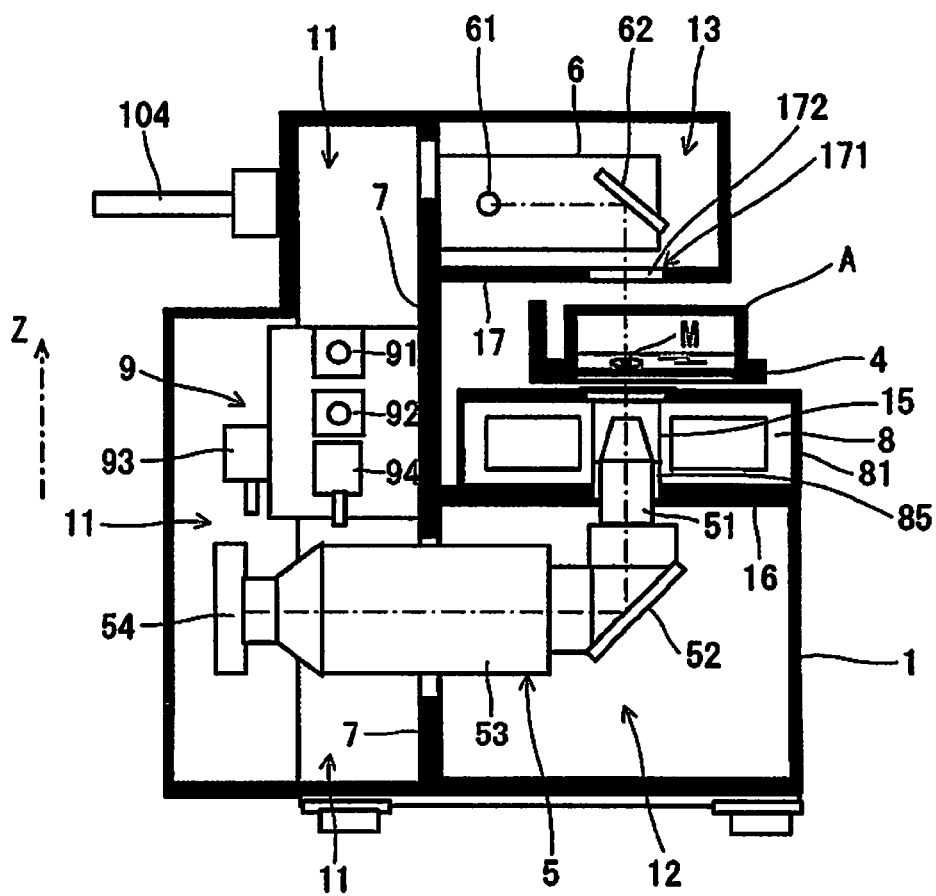
FIG. 6 is a cross-sectional view of the observation unit taken along a VI-VI line shown in FIG. 4.

FIG. 2 is a perspective view showing an appearance of the observation unit. FIGS. 3, 4 and 5 are a side view, a front view, and a rear view of the observation unit respectively. FIG. 6 is a cross-sectional view of the observation unit taken along a VI-VI line shown in FIG. 4.

As shown in FIGS. 2 to 5, the observation unit comprises a casing 1. Outside the casing 1, provided are a placing table 4 on which a fluid vessel A containing the sample is placed, an X-axis drive mechanism 2 for moving the placing table 4 in an X-axis direction, and a Y-axis drive mechanism 3 for moving the placing table 4 in a Y-axis direction. The X-axis direction and the Y-axis direction are two directions perpendicular to each other within a horizontal plane.

As shown in FIG. 6, the casing 1 is provided therein with an observation device 5 for observing the sample in the fluid vessel A, an illuminating device 6 for illuminating the sample in the fluid vessel A, and a drive device 9 for driving the X-axis drive mechanism 2, Y-axis drive mechanism 3 and the observation device 5.

As shown in FIG. 6, the casing 1 is provided with a shielding member 7 preventing heat transfer from a rear surface side to a front surface side, especially heat transmission and heat emission from the rear surface side to the front surface side. On a front surface side of the shielding member 7, the placing table 4 is arranged, while on a rear surface side of the shielding member 7, defined in the casing 1 is a first space 11 located at a position displaced from the placing table 4 in the horizontal direction and extending in a vertical direction with the drive device 9 being contained in the first space 11. Also, on the front surface side of the shielding member 7, defined in the casing 1 are a second space 12 located below the placing table 4 and a third space 13 located above the placing table 4.

Therefore, the shielding member 7 is interposed between the first space 11 located on the rear surface side and the placing table 4, second space 12, and third space 13 located on the front surface side. As a result, the shielding member 7 prevents heat transfer from the first space 11 located on the rear surface side to the placing table 4, second space 12 and third space 13 located on the front surface side.

As shown in FIG. 6, the first to third spaces 11 to 13 are sealed by the shielding member 7 and the casing 1.

As shown in FIG. 6, a hollow heat insulating member 8 is provided on a top surface side of a top surface wall 16 of the casing 1, which forms a top part of the second space 12. The heat insulating member 8 is accommodated in a case 81, and an upper side part of the heat insulating member 8 is in contact with an upper inner surface of the case 81 while a lower side part of the heat insulating member 8 is in contact with a top surface of the top surface wall 16.

Figure 8:
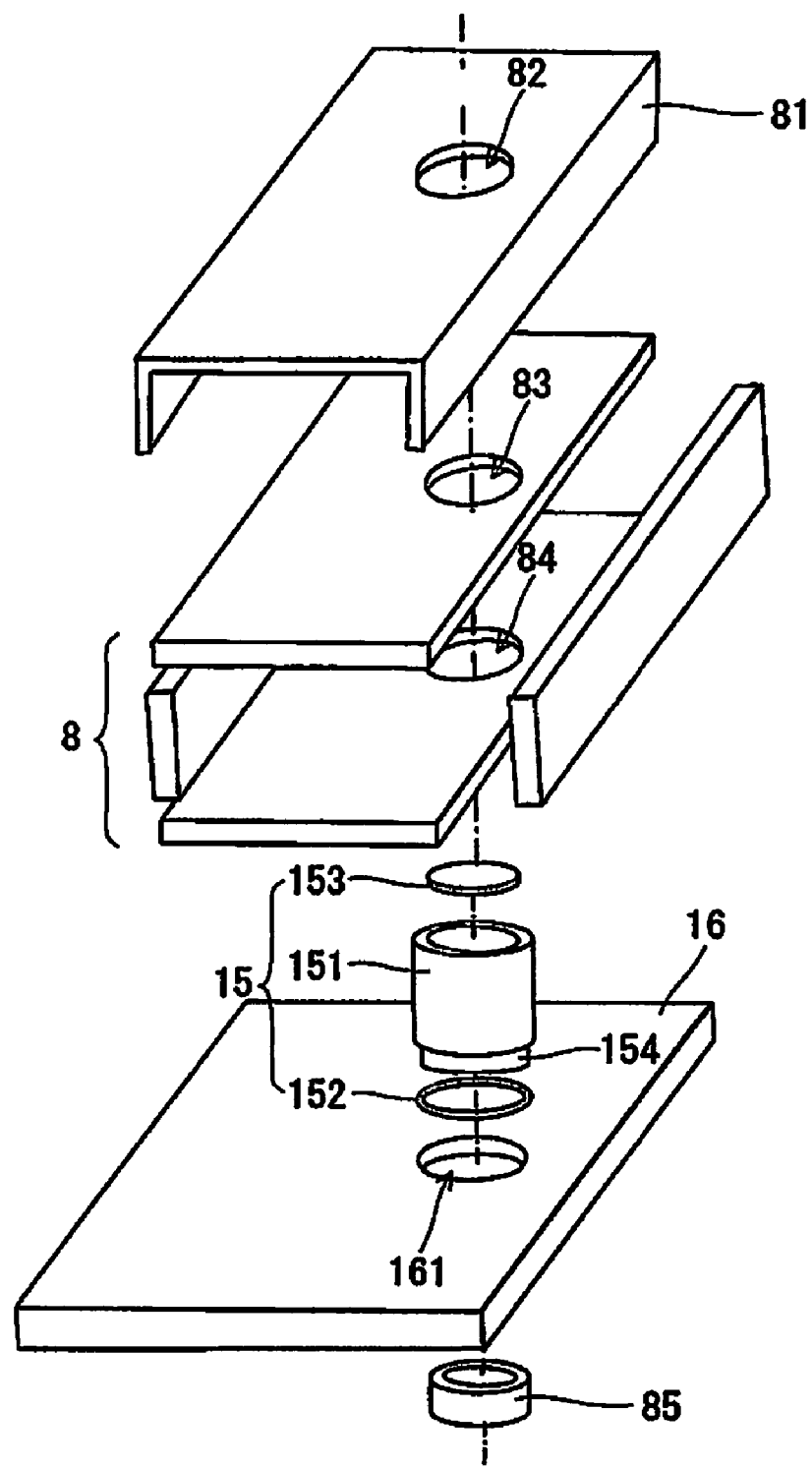
FIG. 8 is an exploded perspective view showing a main part of the observation unit, which is related to a heat insulating member.

As shown in FIG. 8, the case 81, the upper side part of the heat insulating member 8, and the lower side part of the heat insulating member 8 are provided with through-holes 82-84 vertically penetrating these elements.

By providing the heat insulating member 8 on the top surface side of the top surface wall 16, a part of a heat insulating layer is formed between the top surface wall 16 and the placing table 4, thereby inhibiting heat transmission from the top surface wall 16 to the placing table 4.

Between the upper side part and the lower side part of the hollow heat insulating member 8, defined is a gap as shown in FIG. 6. Therefore, the air in the storage 101 flows into the gap, thereby further enhancing heat insulating effect between the top surface wall 16 and the placing table 4.

As shown in FIG. 6, the drive device 9 is arranged in the first space 11 and installed on a rear surface of the shielding member 7.

Figure 7:
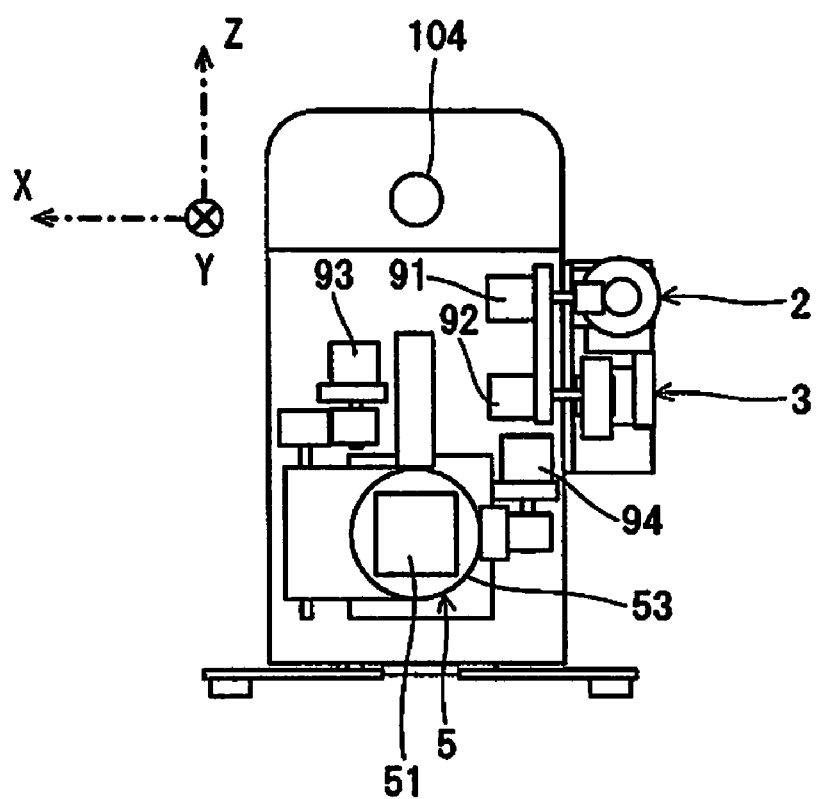
FIG. 7 is a rear view of the observation unit without showing a rear surface wall of a casing.

FIG. 7 is a rear view of the observation unit without showing a rear surface wall of the casing 1. As shown in FIG. 7, the drive device 9 comprises an X-axis motor 91 driving the X-axis drive mechanism 2, a Y-axis motor 92 driving the Y-axis drive mechanism 3, a Z-axis motor 93 for moving the observation device 5 in a Z-axis direction (the vertical direction), and a driving motor 94 driving a zoom lens 53 of the observation device 5.

Both the X-axis motor 91 and the Y-axis motor 92 are arranged so that rotation axes thereof extend along the x-axis direction. Also, both the Z-axis motor 93 and the driving motor 94 are arranged so that rotation axes thereof extend along the z-axis direction.

These motors generate a large amount of heat by rotating.

As shown in FIG. 6, the illuminating device 6 is arranged in the third space 13. The illuminating device 6 comprises an LED (Light Emitting Diode) 61 emitting light and a reflective mirror 62 reflecting light emitted by the LED 61 vertically downward.

A bottom surface wall 17 of the casing 1 forming the third space 13 is provided with a through-hole 171 below the reflective mirror 62. A light transmission plate 172 is fitted in the through-hole 171 with no space therebetween. Therefore, it is possible to guide light reflected by the reflective mirror 62 from the third space 13 to a space where the placing table 4 is arranged, while maintaining the third space 13 in a sealed state.

As shown in FIG. 6, a position through which the light reflected by the reflective mirror 62 passes in the space where the placing table 4 is arranged is an observation point M where the sample is observed by the observation device 5.

As shown in FIG. 6, the observation device 5 is arranged in the first and second spaces 11, 12, and the observation device 5 penetrates the shielding member 7.

The observation device 5 is a phase-contrast microscope and comprises an objective lens 51 forming an enlarged image of the sample which is to be observed, a reflective mirror 52 guiding the enlarged image formed by the objective lens 51 to the zoom lens 53, the zoom lens 53 further enlarging the enlarged image of the sample, and a CCD (Charge Coupled Device) camera 54 imaging an observation image enlarged by the zoom lens 53. An optical system of the observation device 5 is formed by the objective lens 51, the reflective mirror 52, and the zoom lens 53, while an imaging system of the observation device 5 is formed by the CCD camera 54.

In the first space 11, arranged is the CCD camera 54 forming the imaging system of the observation device 5, while in the second space 12, arranged are the objective lens 51, the reflective mirror 52, and the zoom lens 53 which form the optical system of the observation device 5. The objective lens 51 is arranged below the observation point M.

In the observation unit according to this embodiment, since the zoom lens 53 is arranged so as to penetrate the shielding member 7, a part of the zoom lens 53 is inside the first space 11.

An observation magnification for the sample used in the observation device 5 is fixed by a magnification ratio of the objective lens 51 and a magnification ratio of the zoom lens 53. The driving motor 94 is driven to change the magnification ratio of the zoom lens 53, and the observation magnification for the sample can be thereby changed in the observation device 5 according to this embodiment.

From the top surface wall 16 of the casing 1, a light transmission part 15 transmitting light downward from the observation point M to the second space 12 projects at a position below the observation point M. In particular, as shown in FIG. 8, the light transmission part 15 comprises a tubular member 151, a seal ring 152, and a light transmission plate 153. A through-hole 161 for attaching the light transmission part 15 is defined in the top surface wall 16 of the casing 1.

The light transmission plate 153 is fitted in a top end of the tubular member 151 with no space therebetween. A fitting part 154 to be fitted in the through-hole 161 is formed at a bottom end part of the tubular member 151. The fitting part 154 is fitted in the through-hole 161 with the seal ring 152 attached to an outer circumferential surface of the fitting part 154.

As shown in FIGS. 6 and 8, the light transmission part 15 penetrates the through-holes 82-84 of the case 81 and the heat insulating member 8, and the light transmission plate 153 is exposed on a top surface of the case 81.

Therefore, even in the case where the heat insulating member 8 is arranged on the top surface side of the top surface wall 16, the light reflected by the reflective mirror 62 of the illuminating device 6 passes through the light transmission plate 153 of the light transmission part 15 to be guided to the objective lens 51 of the observation device 5.

By attaching the seal ring 152 to the outer circumferential surface of the fitting part 154, covered by the seal ring 152 is a gap defined between an inner circumferential surface forming the through-hole 161 and the outer circumferential surface of the fitting part 154. As a result, the second space 12 is maintained in a sealed state.

As shown in FIG. 6, the objective lens 51 of the observation device 5 is arranged in the light transmission part 15. Therefore, even in the case where a focal point distance of the objective lens 51 is small, it is possible to focus on the sample arranged at the observation point M.

A circular heat insulating member 85 is provided on an inner circumferential surface of the tubular member 151 of the light transmission part 15, and a small gap is defined between the heat insulating member 85 and the objective lens 51. The objective lens 51 can thereby vertically move and heat is thereby inhibited from being transmitted from bottom toward top through the light transmission part 15.

Figure 9:
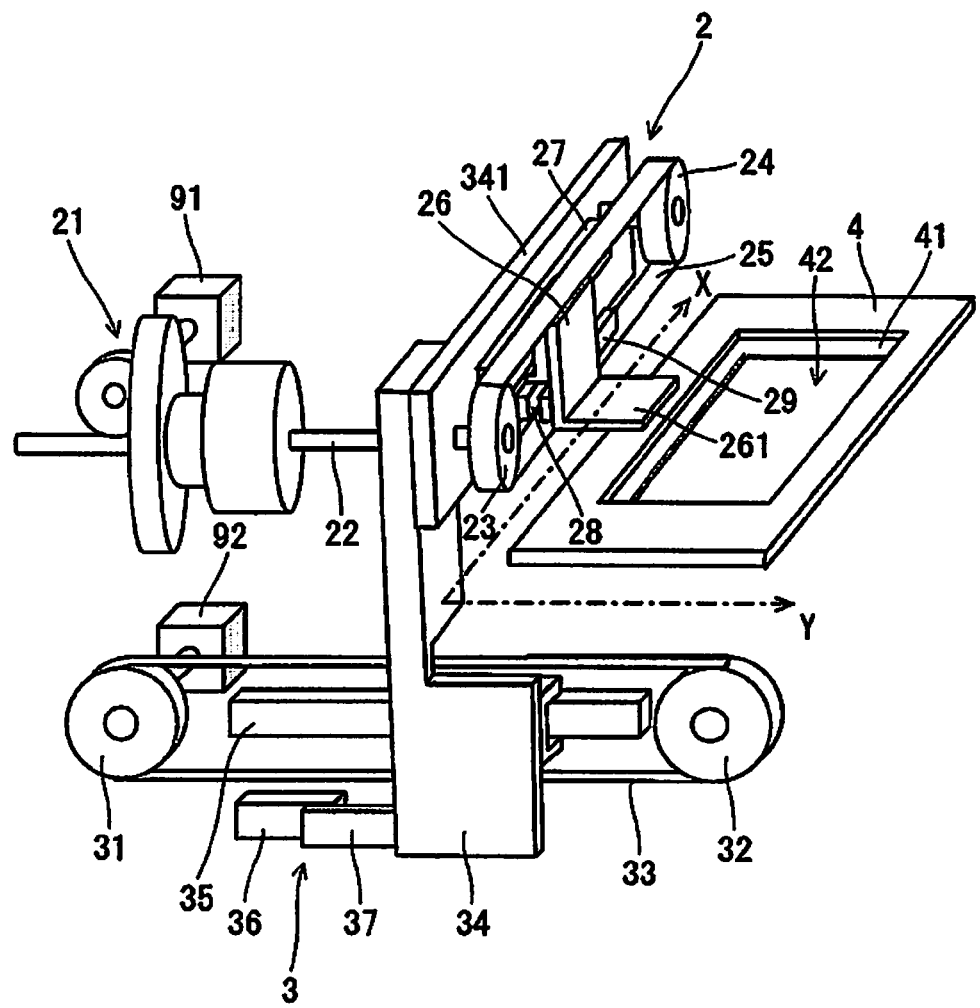
FIG. 9 is a perspective view showing an X-axis drive mechanism and a Y-axis drive mechanism.

FIG. 9 is a perspective view showing the X-axis drive mechanism 2 and the Y-axis drive mechanism 3. The Y-axis drive mechanism 3 comprises a pair of pulleys 31, 32, a timing belt 33, a Y-axis slide body 34 having an inverted L-shape, and a guiding member 35, as shown in FIG. 9. One pulley 31 of the pair of pulleys 31, 32 is fixed to a rotation axis of the Y-axis motor 92, and the one pulley 31 rotates around the rotation axis of the Y-axis motor 92 in accordance with the rotation of the Y-axis motor 92.

The other pulley 32 is rotatably arranged at a position displaced from the position of the one pulley 31 in the Y-axis direction.

Figure 10:
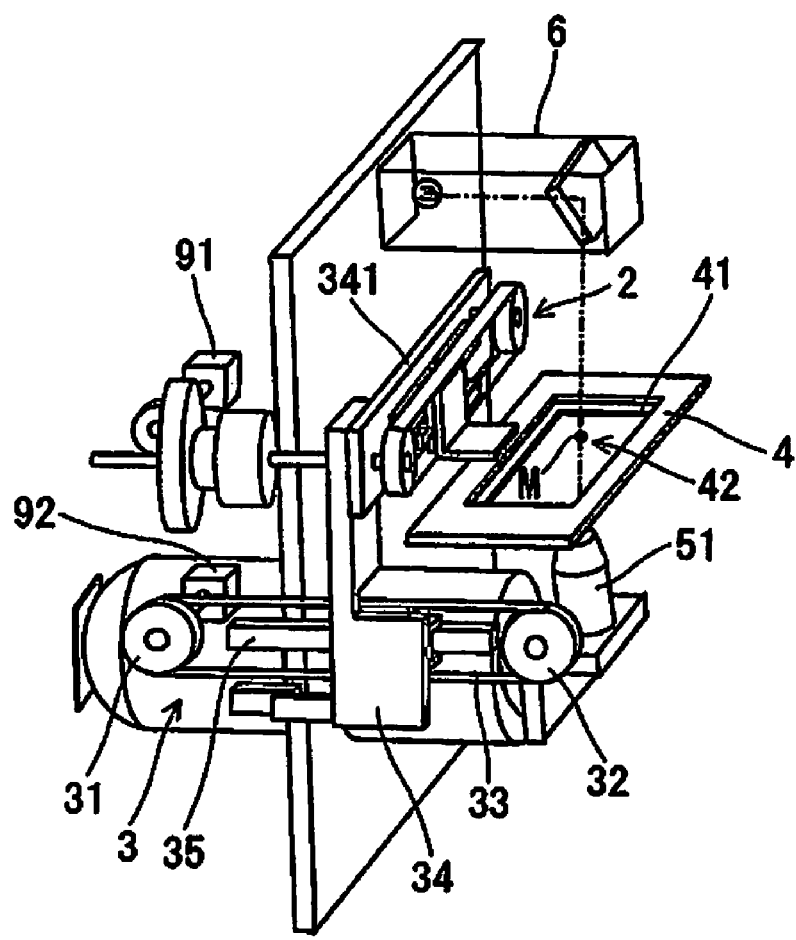
FIG. 10 is a perspective view showing arrangement of a Y-axis slide body forming the Y-axis drive mechanism.

The timing belt 33 is entrained about the pair of pulleys 31, 32. The Y-axis slide body 34 is coupled to the timing belt 33 at a position between the pair of pulleys 31, 32. As shown in FIG. 10, the Y-axis slide body 34 is arranged so that an upper side part 341 thereof is located along the x-axis direction in the space where the placing table 4 is arranged. Also, the Y-axis slide body 34 is slidably coupled to the guiding member 35, and therefore, a path on which the Y-axis slide body 34 can move is defined along the Y-axis direction.

When the one pulley 31 rotates, the timing belt 33 thereby rotates. At this time, a part of the timing belt 33 which is located between the pair of pulleys 31, 32 moves along the Y-axis direction, and therefore, rotational motion of the one pulley 31 is converted into translational motion in the Y-axis direction by the timing belt 33.

Accordingly, rotational force of the Y-axis motor 92 is converted into translational force in the Y-axis direction by the Y-axis drive mechanism 3 to be given to the Y-axis slide body 34. As a result, the Y-axis slide body 34 moves along the Y-axis direction.

As shown in FIG. 9, the X-axis drive mechanism 2 comprises a gear mechanism 21, a shaft 22 extending in the Y-axis direction, a pair of pulleys 23, 24, a timing belt 25, an X-axis slide body 26 having an L-shape, and a guiding member 27.

The gear mechanism 21 converts rotational force of the X-axis motor 91 into rotational force around a center axis of the shaft 22 to give the converted rotational force to the shaft 22. The shaft 22 is rotatably supported on the upper side part 341 of the Y-axis slide body 34 of the Y-axis drive mechanism 3, and is rotated around the center axis by the rotational force given by the gear mechanism 21. The shaft 22 is slidable with respect to the gear mechanism 21.

One pulley 23 of the pair of pulleys 23, 24 is fixed to one end of the shaft 22, and the one pulley 23 rotates around the axis shared with the shaft 22 in accordance with the rotation of the shaft 22.

The other pulley 24 is rotatably attached to the upper side part 341 of the Y-axis slide body 34 at a position displaced from the position of the one pulley 23 in the x-axis direction.

The timing belt 25 is entrained about the pair of pulleys 23, 24. The X-axis slide body 26 is coupled to the timing belt 25 at a position between the pair of pulleys 23, 24. The X-axis slide body 26 is slidably coupled to the guiding member 27, and therefore, a path on which the X-axis slide body 26 can move is defined along the X-axis direction.

The placing table 4 is fixed to a lower side part 261 of the X-axis slide body 26.

When the one pulley 23 rotates, the timing belt 25 thereby rotates. At this time, a part of the timing belt 25 which is located between the pair of pulleys 23, 24 moves along the X-axis direction, and therefore, rotational motion of the one pulley 23 is converted into translational motion in the X-axis direction by the timing belt 25.

Accordingly, rotational force of the X-axis motor 91 is converted into translational force in the X-axis direction by the X-axis drive mechanism 2 to be given to the X-axis slide body 26. As a result, the X-axis slide body 26 moves along the X-axis direction.

Therefore, with the X-axis drive mechanism 2 and the Y-axis drive mechanism 3, the placing table 4 fixed to the X-axis slide body 26 is moved along the X-axis direction by rotation of the X-axis motor 91, and is moved along the Y-axis direction by rotation of the Y-axis motor 92. Thus, the X-axis drive mechanism 2 and the Y-axis drive mechanism 3 form a transmitting member transmitting drive force of the X-axis motor 91 and the Y-axis motor 92 to the placing table 4.

Further, as shown in FIG. 9, the X-axis drive mechanism 2 is provided with an X-axis sensor 28 and an X-axis sensor plate 29, while the Y-axis drive mechanism 3 is provided with a Y-axis sensor 36 and a Y-axis sensor plate 37.

The X-axis sensor plate 29 is fixed to the X-axis slide body 26 and moves in the X-axis direction in accordance with movement of the X-axis slide body 26. The Y-axis sensor plate 37 is fixed to the Y-axis slide body 34 and moves in the Y-axis direction in accordance with movement of the Y-axis slide body 34.

The X-axis sensor 28 is switched ON/OFF by approach/estrangement of the X-axis sensor plate 29. The X-axis sensor 28 is switched ON when the X-axis sensor plate 29 faces the X-axis sensor 28. Thus, the X-axis sensor 28 and the X-axis sensor plate 29 form a detection part and a to-be-detected part which is to be detected by the detection part.

The X-axis sensor 28 is arranged so that when the X-axis sensor plate 29 faces the X-axis sensor 28 to switch the X-axis sensor 28 ON, a center C of the fluid vessel A placed on the placing table 4 matches the observation point M in the X-axis direction.

The Y-axis sensor 36 is switched ON/OFF by approach/estrangement of the Y-axis sensor plate 37. The Y-axis sensor 36 is switched ON when the Y-axis sensor plate 37 faces the Y-axis sensor 36. Thus, the Y-axis sensor 36 and the Y-axis sensor plate 37 form a detection part and a to-be-detected part which is to be detected by the detection part.

The Y-axis sensor 36 is arranged so that when the Y-axis sensor plate 37 faces the Y-axis sensor 36 to switch the Y-axis sensor 36 ON, the center C of the fluid vessel A placed on the placing table 4 matches the observation point M in the Y-axis direction.

Accordingly, even in the case where the center C of the fluid vessel A is located at a position displaced from the observation point M, the center C of the fluid vessel A can easily return to the observation point M.

In the observation unit according to this embodiment, the Y-axis drive mechanism 3 is arranged below the placing table 4 as shown in FIG. 3, and therefore, it is possible to increase range of motion of the placing table 4 in the X-axis direction. Also, it is possible to place the fluid vessel A which is large in size on the placing table 4.

Also, in the observation unit according to this embodiment, since the Y-axis slide body 34 having the inverted L-shape is used as shown in FIG. 9, it is possible to move the placing table 4 in the X-axis direction and Y-axis direction only by providing the Y-axis drive mechanism 3 on one side of the X-axis drive mechanism 2. Therefore, it is easy to place the fluid vessel A on the placing table 4.

As shown in FIG. 9, on a top surface of the placing table 4, defined is a fitting groove 41 in which the fluid vessel A is to fit in order to prevent displacement of the fluid vessel A placed on the top surface. The fitting groove 41 has a shape which is slightly larger than that of the fluid vessel A to be placed.

A through-hole 42 is defined in a bottom surface of the fitting groove 41 in a central area thereof. It is thereby possible that the light reflected by the reflective mirror 62 of the illuminating device 6 passes through the through-hole 42 to enter the objective lens 51 of the observation device 5 as shown in FIG. 10. Therefore, the placing table 4 does not prevent observation of the sample in the fluid vessel A placed on the placing table 4.

Figure 11:
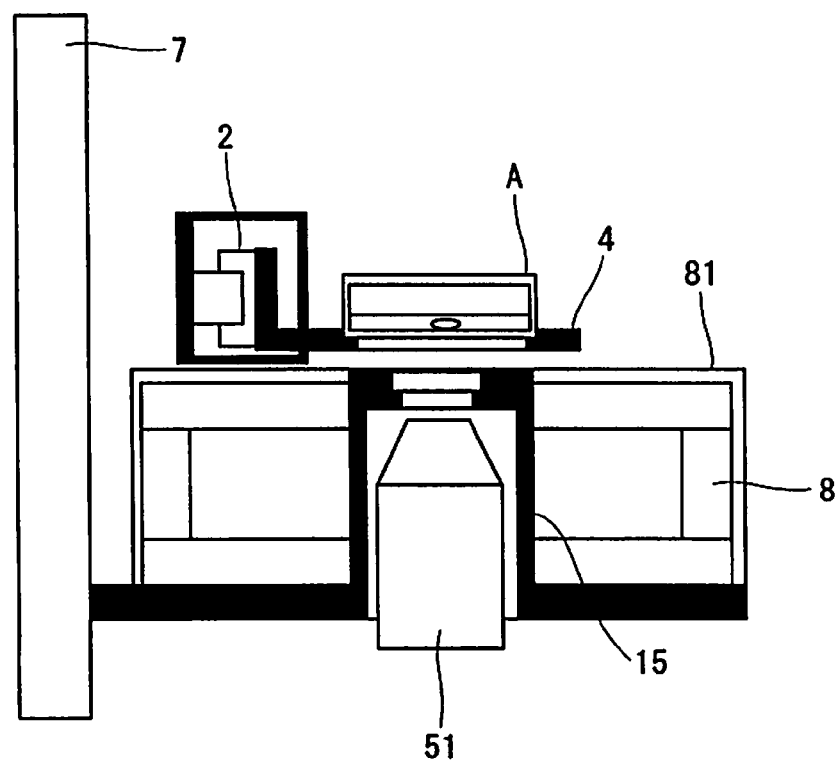
FIG. 11 is a cross-sectional view showing a placing state of a placing table.

FIG. 11 is a cross-sectional view showing a placing state of the placing table 4. As shown in FIG. 11, the placing table 4 is coupled to the X-axis drive mechanism 2 with a bottom surface of the placing table 4 separated from the top surface of the case 81. Therefore, the air exists between the bottom surface of the placing table 4 and the top surface of the case 81, and the air functions as the heat insulating layer. Accordingly, inhibited is heat transmission from the case 81 to the placing table 4.

Also, by slightly separating the bottom surface of the placing table 4 from the top surface of the case 81, it is possible to focus the objective lens 51 on the sample in the fluid vessel A placed on the placing table 4, and prevent friction due to sliding movement between the placing table 4 and the case 81 even when the placing table 4 is moved. Accordingly, inhibited is vibration of the placing table 4 caused by the friction.

Figure 12:
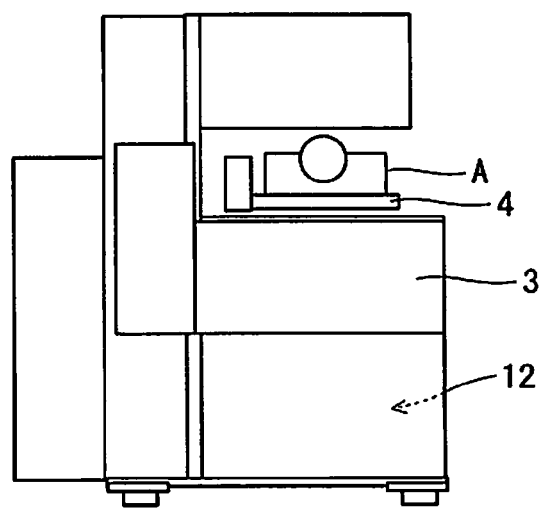
FIG. 12 is a side view showing the placing table arranged at an observation position.
Figure 13:
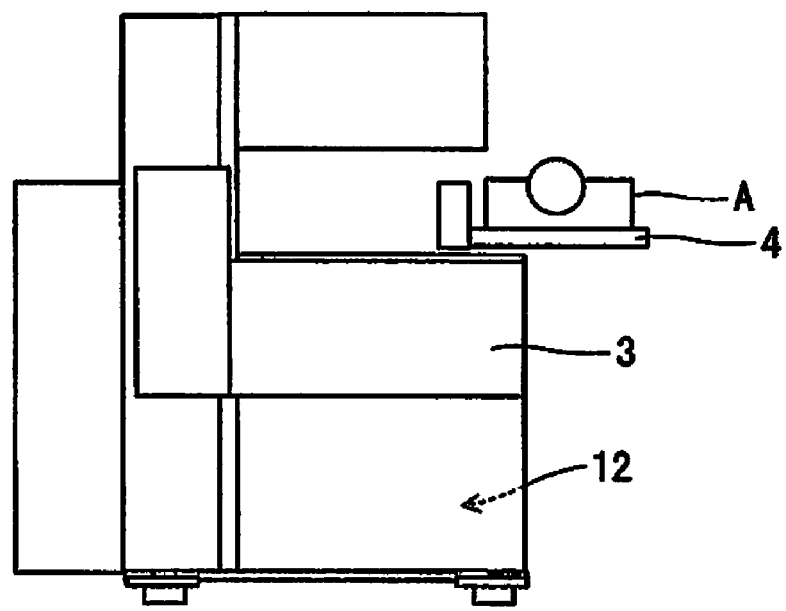
FIG. 13 is a side view showing the placing table arranged at a separated position.

FIG. 12 is a side view showing the placing table 4 arranged at an observation position, while FIG. 13 is a side view showing the placing table 4 arranged at a separated position. By driving the Y-axis drive mechanism 3, the placing table 4 can reciprocate between the observation position where the sample in the fluid vessel A is observed as shown in FIG. 12 and the separated position which is separated in the Y-axis direction from a position above the second space 12 as shown in FIG. 13.

Although the placing table 4 is separated from the position above the second space 12 in the Y-axis direction in the observation unit according to this embodiment, a configuration of the X-axis drive mechanism 2 can be modified so that the placing table 4 can be separated from the position above the second space 12 in the X-axis direction.

The observation unit described above has a configuration which can be downsized, and therefore, the observation unit can be downsized such a degree that the observation unit can be taken into and from the storage 101 which is small in size. Therefore, the observation unit described above has a high applicability. Further, since the observation unit can be taken into and from the storage 101, it is possible to clean an interior of the storage 101 with the observation unit taken therefrom.

In the observation unit described above, the drive device 9, the observation device 5, and the illuminating device 6 are provided inside the space (the first to third spaces 11 to 13) sealed by the casing 1. Therefore, even in the case where the observation unit is installed in the storage 101, the drive device 9, the observation device 5, and the illuminating device 6 are not exposed to the environment in the storage 101. Therefore, the drive device 9, the observation device 5, and the illuminating device 6 hardly cause troubles due to moisture or the like even in the case where the observation unit is used in the storage 101.

Further, since the heat generated in the drive device 9 is conducted to the ambient air to rise together with the air, the heat of the drive device 9 is hardly conducted to the placing table 4 arranged at a position displaced from the drive device 9 in the horizontal direction. Accordingly, the heat is hardly conducted to the sample placed on the placing table 4, resulting in inhibition of temperature increase of the sample due to heat transmission. Therefore, it is possible to observe the sample in the storage 101 without subjecting the sample to the influence of heat such that cultivation of the sample is prevented, the sample is killed, or the like.

The heat which rose together with the air is diffused from a top part of the casing 1. Therefore, it is preferable to provide a heat radiation fin or the like on the top part of the casing 1, whereby the heat in the casing 1 is diffused effectively.

In the case where the observation unit is installed in the storage 101, the heat in the casing 1 is diffused from the top part of the casing 1 into the storage 101 to be conducted to the air in the storage 101. However, since temperature of the air in the storage 101 is controlled by a heater or the like, the heat diffused from the top part of the casing 1 causes little change in the temperature in the storage 101, and therefore, the sample stored in the storage 101 is not affected.

In the observation unit described above, the shielding member 7 is interposed between the first space 11 and the placing table 4, and between the first space 11 and the second space 12. Therefore, the heat generated in the drive device 9 in the first space 11 and the imaging system of the observation device 5 is prevented from being transferred to the placing table 4 and the second space 12 by the shielding member 7, especially heat transmission and heat emission from the first space 11 to the placing table 4 and the second space 12 are prevented by the shielding member 7. Therefore, even in the case where heat is generated in the drive device 9 and the imaging system of the observation device 5, the temperature of the sample scarcely increases. Accordingly, it is possible to observe the sample in the storage 101 without subjecting the sample to the influence of heat.

Although the sample to be observed is illuminated by the light emitted by the LED 61 of the illuminating device 6, the LED 61 is turned on only when the sample is searched or imaged (at the time of shutter operation) in a time lapse observation to be described later, and therefore, the sample is scarcely affected by heat.

In the observation unit described above, between the top surface wall 16 of the casing 1 and the placing table 4, the heat insulating layer is formed by the heat insulating member 8 and the air. Therefore, even in the case where the heat generated in the drive device 9, the imaging system of the observation device 5, and the illuminating device 6 is conducted through the casing 1 to reach the top surface wall 16, the heat is hardly transmitted to the placing table 4, resulting in inhibition of temperature increase of the sample due to heat conduction. Accordingly, it is possible to observe the sample in the storage 101 without subjecting the sample to the influence of heat.

Also, in the observation unit described above, the placing table 4 can reciprocate between the observation position and the separated position, and therefore, by arranging the placing table 4 at the separated position, it is possible to distance the placing table 4 from a heat source such as the drive device 9, the imaging system of the observation device 5, the illuminating device 6 and the like. Accordingly, by moving the placing table 4 to the separated position, it is possible to inhibit heat transfer from the heat source to the sample, and arrange the sample under the environment in the storage 101.

Further, in the observation unit described above, it is possible to move the placing table 4 along the X-axis direction by rotating the X-axis motor 91 while move the placing table 4 along the Y-axis direction by rotating the Y-axis motor 92. Therefore, by controlling rotational rate and rotation amount of the X-axis motor 91 and the Y-axis motor 92 by the control device 102, it is possible to automate drive of the placing table 4.

3. Time Lapse Observation by Observation Unit

Figure 14:
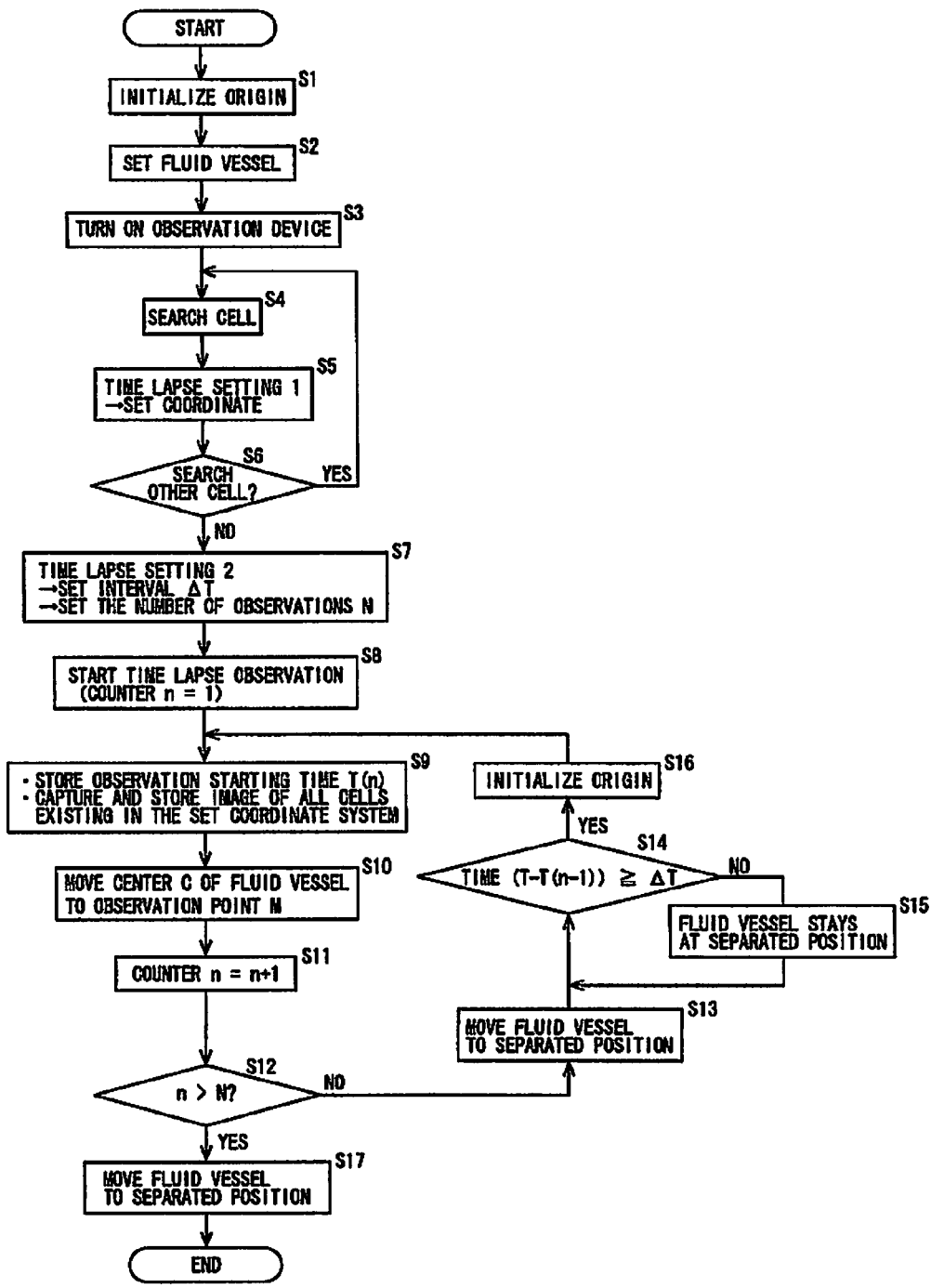
FIG. 14 is a flow chart showing a flow of a time lapse observation performed by the observation unit.

FIG. 14 is a flow chart of time lapse observation of the sample performed by the observation unit described above. Here, the time lapse observation is an observation method in which a sample is observed a plurality of times repeatedly at a set interval ΔT to obtain an observation image of the sample every time of the observation. Following is a description of a case where a cell is contained in the fluid vessel A as the sample.

First, in step S1, an origin O of an X-Y coordinate system set for the fluid vessel A is initialized. In particular, the X-Y coordinate system is set for the fluid vessel A while setting the origin O at a position where the observation point M exists in a state where both the X-axis sensor 28 and the Y-axis sensor 36 are ON.

Then, in step S2, the fluid vessel A is placed on the placing table 4. Thereafter in step S3, a power of the observation device 5 is turned ON, and then in step S4, the cell which is to be observed in the time lapse observation is searched. In step S4, the observer moves the placing table 4 to search the cell while seeing an image displayed on display means of the personal computer 103.

Once the cell to be observed is found, a position of the cell in the X-Y coordinate system and the observation magnification are inputted by using inputting means of the personal computer 103 in step S5. A coordinate and the observation magnification of the cell to be observed are thereby set (time lapse setting 1). The coordinate and the observation magnification set here are given to the control device 102.

In the case where a plurality of cells are to be observed, the flow returns from step S6 to step S4 and executes step S4 and step S5 repeatedly.

After completing the coordinate setting for all the cells to be observed, the interval ΔT for executing the time lapse observation and the number of observations N are inputted using the inputting means of the personal computer 103 in step S7. The interval ΔT and the number of observations N are thereby set (time lapse setting 2). The interval ΔT and the number of observations N set here are given to the control device 102.

Once the time lapse setting in step S7 is completed, the time lapse observation starts in step S8. Here, a value of a counter n is set to one in the control device 102.

Then, in step S9, observation starting time T(n) is stored in storing means of the control device 102, and the observation of all the cells existing in the coordinates set in step S5 is automatically performed by the observation unit under control of the control device 102. In particular, the cell located at each set coordinate is guided to the observation point M, and the observation of the cell is executed by the observation device 5 at the observation magnification set in step S5. The observation image of each observed cell is imaged by the CCD camera 54 of the observation device 5, and the image thereby captured is stored in storing means of the personal computer 103.

After completion of the observation of the cell in step S9, the control device 102 moves the center C of the fluid vessel A to the observation point M so that both the X-axis sensor 28 and the Y-axis sensor 36 are ON in step S10. Then, in step S11, the value of the counter n is increased by one, and then in step S12, the control device 102 determines whether or not the value of the counter n exceeds the number of observations N set in step S7.

If the control device 102 determines that the value of the counter n does not exceed the number of observations N in step S12, the control device 102 moves the fluid vessel A to the separated position in step S13. And then, in step S14, the control device 102 calculates elapsed time (T−T(n−1)) from a previous observation starting time T(n−1) until time when the flow goes to step S14, and determines whether or not this elapsed time reaches the interval ΔT set in step S7.

If the control device 102 determines that the elapsed time does not reach the interval ΔT in step S14, the control device 102 keeps the fluid vessel A at the separated position in step S15.

In contrast, if the control device 102 determines that the elapsed time reaches the interval ΔT in step S14, the control device 102 initializes the origin O of the X-Y coordinate system set for the fluid vessel A in step S16 in the same manner as in step S1, and then the flow returns to step S9 to execute the observation of the cell again.

Then, the observation of the cell is repeatedly executed until the control device 102 determines that the value of the counter n exceeds the number of observations N in step S12.

If the control device 102 determines that the value of the counter n exceeds the number of observations N in step S12, the control device 102 moves the fluid vessel A to the separated position in step S13 and ends the time lapse observation.

By utilizing the image of the cell obtained in the time lapse observation described above, it is possible to observe and analyze growing condition or shape of the cell.

4. Modification 4-1. First Modification

Figure 15:
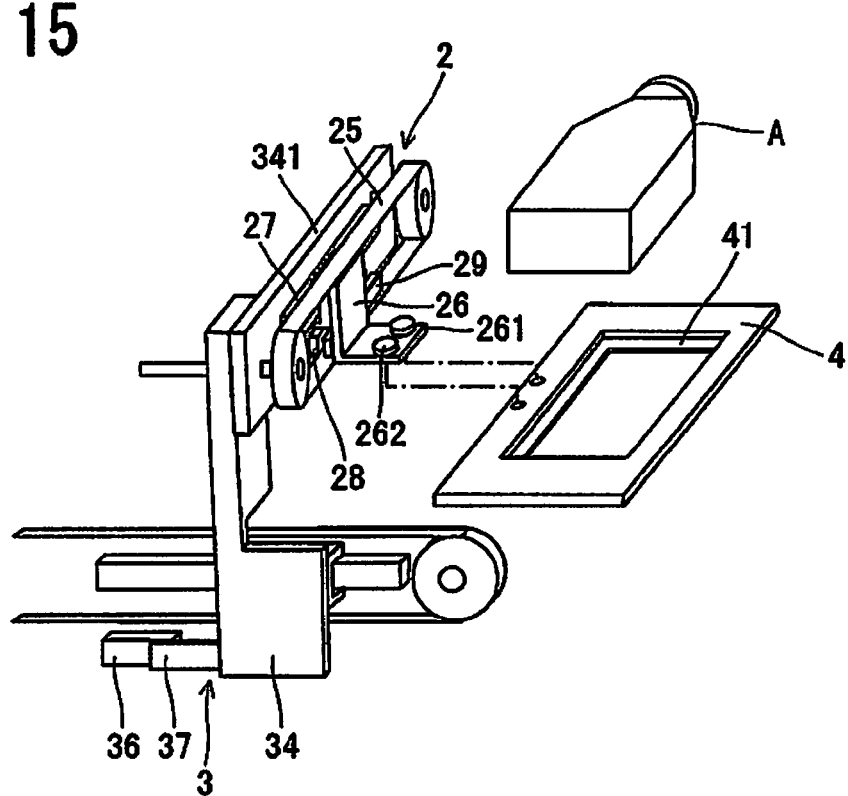
FIG. 15 is a perspective view showing attachment of the placing table provided with a quadrangular fitting groove in an observation unit according to a first modification.
Figure 16:
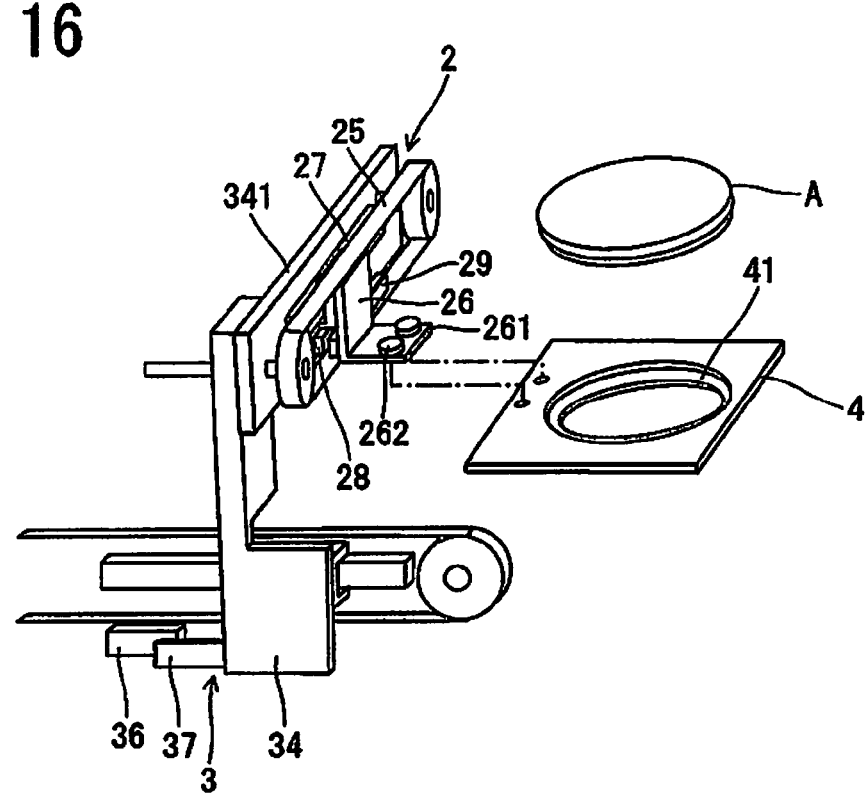
FIG. 16 is a perspective view showing attachment of the placing table provided with a circular fitting groove in the observation unit according to the first modification.

FIG. 15 is a perspective view showing attachment of the placing table 4 provided with the fitting groove 41 which has a quadrangular shape in an observation unit according to a first modification. FIG. 16 is a perspective view showing attachment of the placing table 4 provided with the fitting groove 41 which has a circular shape in the observation unit according to the first modification. As shown in FIGS. 15 and 16, the placing table 4 can be removably attached to a lower side part 261 of the X-axis slide body 26 by a screw member 262. Therefore, by preparing a plurality of placing tables 4 provided with the fitting grooves 41 having different shapes, it is possible to select and attach the placing table 4 in accordance with a shape of the fluid vessel A to be used.

In this modification, prepared are the placing table 4 provided with the quadrangular fitting groove 41 to be fitted in by the fluid vessel A having the quadrangular shape as shown in FIG. 15, and the placing table 4 provided with the circular fitting groove 41 to be fitted in by the fluid vessel A having the circular shape as shown in FIG. 16.

Here, if a total weight of the placing table 4 and the fluid vessel A placed on the placing table 4 is different among the plurality of placing tables 4 with the fitting grooves 41 having different shapes, an inertia moment applied to a motor when moving the placing table 4 changes, and therefore, it is possible to cause a change in acceleration or displacement from a target position of the placing table 4.

Therefore, it is preferable that the total weight of the placing table 4 and the fluid vessel A placed on the placing table 4 is nearly uniform among the plurality of placing tables 4 provided with the fitting grooves 41 having different shapes.

Also, it is preferable that a center of gravity of the placing table 4 with the fluid vessel A placed thereon matches a position where the X-axis slide body 26 is coupled thereto in the X-axis direction. Even in the case where the placing table 4 is attached to the X-axis slide body 26 by the screw member 262, the attached placing table 4 is thereby easily stabilized.

4-2. Second Modification

Figure 17:
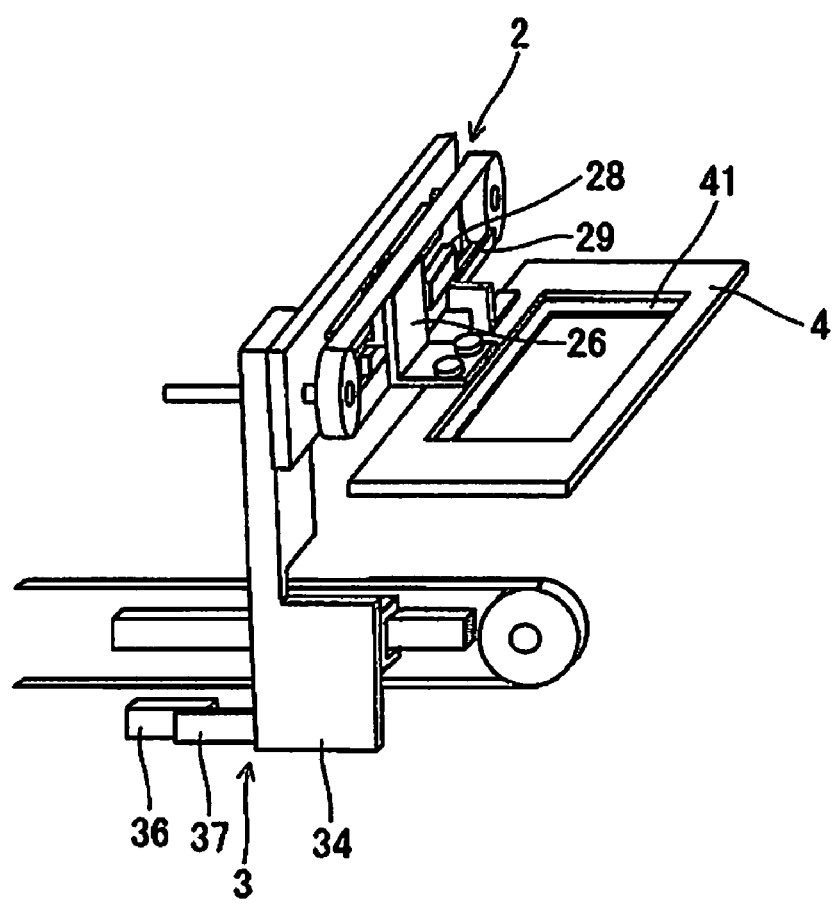
FIG. 17 is a perspective view showing an X-axis sensor plate attached to the placing table provided with the quadrangular fitting groove in an observation unit according to a second modification.
Figure 18:
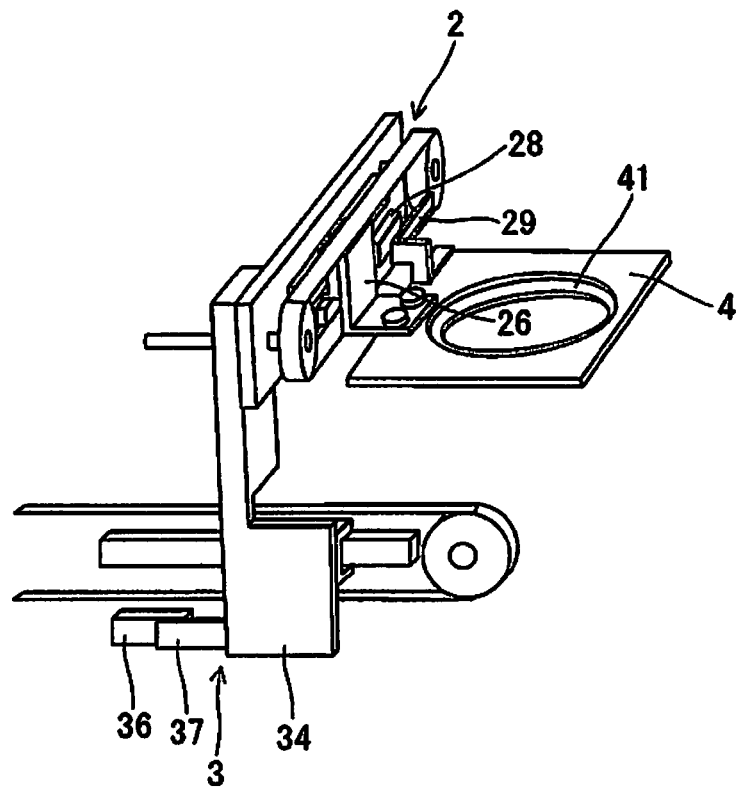
FIG. 18 is a perspective view showing the X-axis sensor plate attached to the placing table provided with the circular fitting groove in the observation unit according to the second modification.
Figure 19:
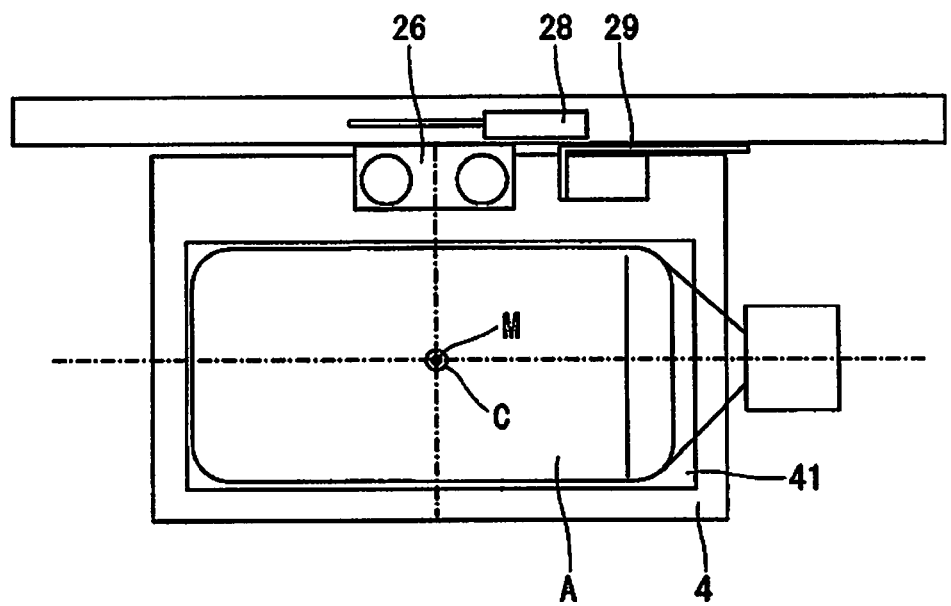
FIG. 19 is a plane view showing the placing table provided with the quadrangular fitting groove in a state where a center of a fluid vessel placed on the placing table matches an observation point.
Figure 20:
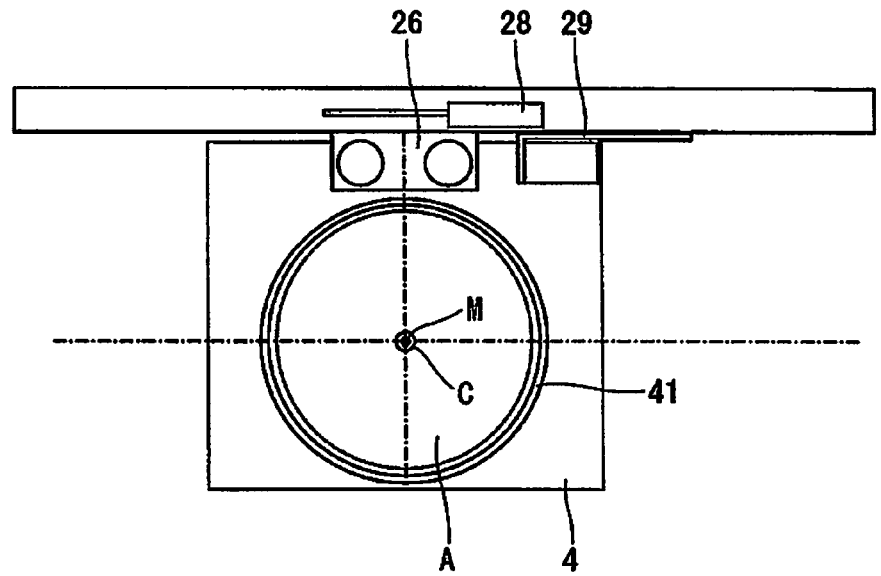
FIG. 20 is a plane view showing the placing table provided with the circular fitting groove in a state where the center of the fluid vessel placed on the placing table matches the observation point.

FIG. 17 is a perspective view showing attachment of the placing table 4 provided with the quadrangular fitting groove 41 in an observation unit according to a second modification, while FIG. 19 is a plane view showing a state where the center C of the fluid vessel A placed on the placing table 4 matches the observation point M. FIG. 18 is a perspective view showing attachment of the placing table 4 provided with the circular fitting groove 41 in the observation unit according to the second modification, while FIG. 20 is a plane view showing a state where the center C of the fluid vessel A placed on the placing table 4 matches the observation point M.

In the case where the placing table 4 can be replaceable as in the first modification described above, in the placing tables 4 provided with the fitting grooves 41 having different shapes, the center of gravity of the placing table 4 with the fluid vessel A placed thereon does not necessarily match the center C of the fluid vessel A. Therefore, in the case where the center of gravity of the placing table 4 with the fluid vessel A placed thereon is matched to the position where the X-axis slide body 26 is coupled thereto in the X-axis direction, as described in the first modification above, the position of the X-axis slide body 26 when the center C of the fluid vessel A matches the observation point M is different among the placing tables 4 provided with the fitting grooves 41 having different shapes.

Therefore, in the case where the X-axis sensor 28 and the X-axis sensor plate 29 of the X-axis drive mechanism 2 are arranged so that the center C of the quadrangular fluid vessel A placed on the placing table 4 shown in FIG. 15 matches the observation point M, if the placing table 4 is replaced with the placing table 4 shown in FIG. 16, the center C of the circular fluid vessel A placed on the placing table 4 is displaced from the observation point M.

Accordingly, it was necessary to rearrange the X-axis sensor 28 and the X-axis sensor plate 29 of the X-axis drive mechanism 2 so that the center C of the circular fluid vessel A placed on the placing table 4 shown in FIG. 16 matches the observation point M.

Here, in the Y-axis direction, the observation unit is designed so that the center of gravity of the placing table 4 with the fluid vessel A placed thereon matches the center C of the fluid vessel A, as to the placing tables 4 provided with the fitting grooves 41 having different shapes. Therefore, it is not necessary to rearrange the Y-axis sensor 36 and the Y-axis sensor plate 37 of the Y-axis drive mechanism 3 even in the case where the placing table 4 is replaced.

In this modification, as shown in FIGS. 17 and 18, the X-axis sensor plate 29 is attached to the placing table 4. Also, the X-axis sensor plate 29 is arranged so that the center C of the fluid vessel A placed on the placing table 4 matches the observation point M when the X-axis sensor plate 29 faces the X-axis sensor 28 as shown in FIGS. 19 and 20, as to each of the placing tables 4 provided with the fitting grooves 41 having different shapes.

Accordingly, even when the placing table 4 is replaced with the placing table 4 provided with the fitting groove 41 having a different shape, it is possible to easily match the center C of the fluid vessel A to the observation point M.

4-3. Third Modification

Figure 21:
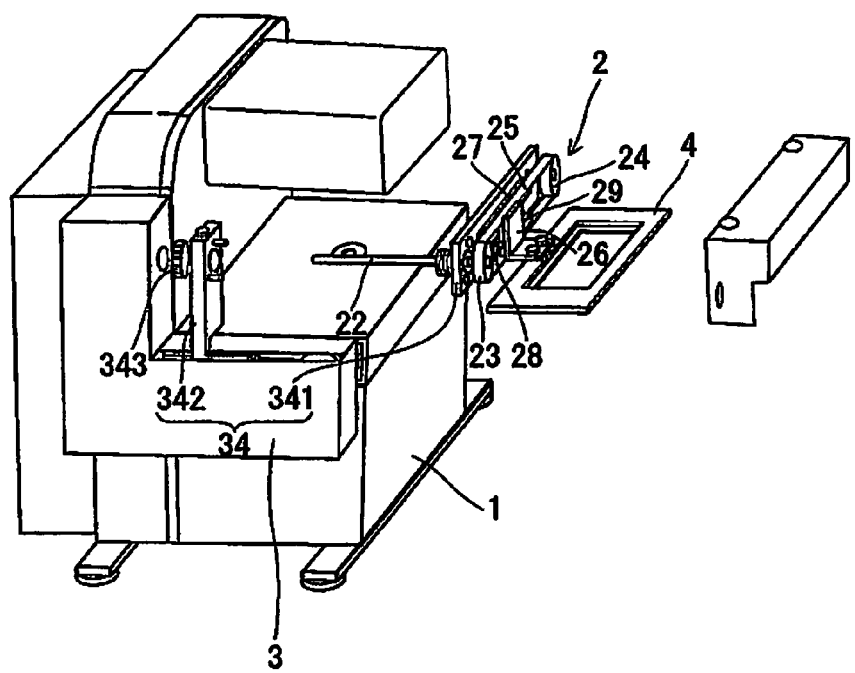
FIG. 21 is an exploded perspective view of an observation unit according to a third modification.

FIG. 21 is an exploded perspective view of an observation unit according to a third modification. As shown in FIG. 21, the X-axis drive mechanism 2 can be removably provided to the observation unit. In particular, the upper side part 341 of the Y-axis slide body 34 of the Y-axis drive mechanism 3 is removably coupled to an upright part 342 by a screw member 343. By separating the upper side part 341 from the upright part 342, detached from the observation unit are the shaft 22, the pair of pulleys 23, 24, the timing belt 25, the X-axis slide body 26, the guiding member 27, the X-axis sensor 28, and the X-axis sensor plate 29 of the X-axis drive mechanism 2 provided to the upper side part 341, and the placing table 4 attached to the X-axis slide body 26.

In the observation unit of this modification, by detaching the X-axis drive mechanism 2, a part covered by the X-axis drive mechanism 2 can be easily cleaned.

4-4. Fourth Modification

Figure 22:
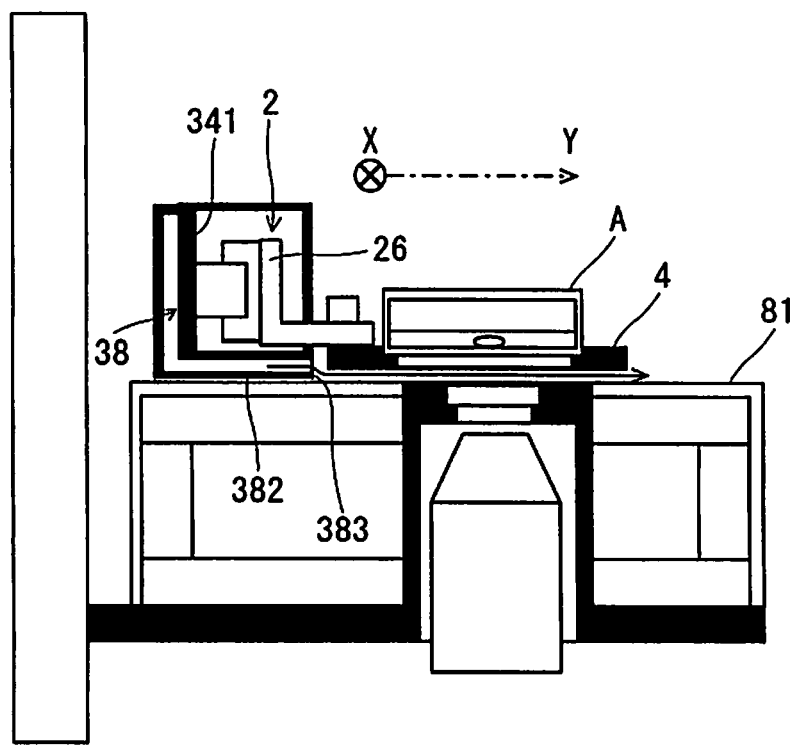
FIG. 22 is a cross-sectional view of a main part of an observation unit according to a fourth modification.
Figure 23:
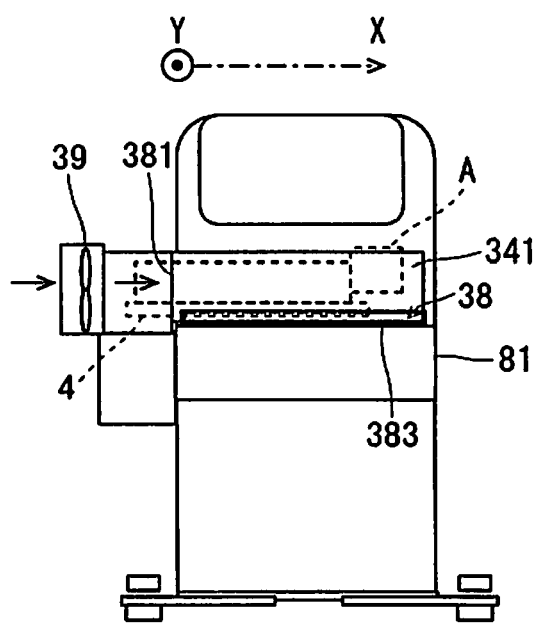
FIG. 23 is a front view of the observation unit according to the fourth modification.

FIG. 22 is a cross-sectional view of an observation unit according to a fourth modification, while FIG. 23 is a front view of this observation unit. As shown in FIGS. 22 and 23, the air can be flowed between the bottom surface of the placing table 4 and the top surface of the case 81 separated from each other. In particular, as shown in FIG. 22, a ventilation opening 38 having an L-shaped cross-section perpendicular to the X-axis direction is defined on a rear surface side and a bottom surface side of the upper side part 341 of the Y-axis slide body 34. The ventilation opening 38 includes openings at a side end 381 (see FIG. 23) and at a front end 383 of a lower side part 382. As shown in FIG. 23, a blowing fan 39 sending the air into the ventilation opening 38 is provided on the side end 381 side of the ventilation opening 38.

With the observation unit according to this modification, the blowing fan 39 sends the air into the ventilation opening 38, whereby the air passes through the ventilation opening 38 to be blown out from the front end 383 of the lower side part 382, and then flows forward (in the Y-axis direction) between the bottom surface of the placing table 4 and the top surface of the case 81.

Since the air flows between the bottom surface of the placing table 4 and the top surface of the case 81, heat transmission from the case 81 to the placing table 4 is inhibited more easily than in the case where the air stays between the bottom surface of the placing table 4 and the top surface of the case 81.

Also, in the observation unit according to this modification, by providing a plurality of grooves extending in the Y-axis direction on the top surface of the case 81, it becomes easier for the air to flow between the bottom surface of the placing table 4 and the top surface of the case 81, whereby heat transmission from the case 81 to the placing table 4 is inhibited even more easily.

4-5. Fifth Modification

Figure 24:
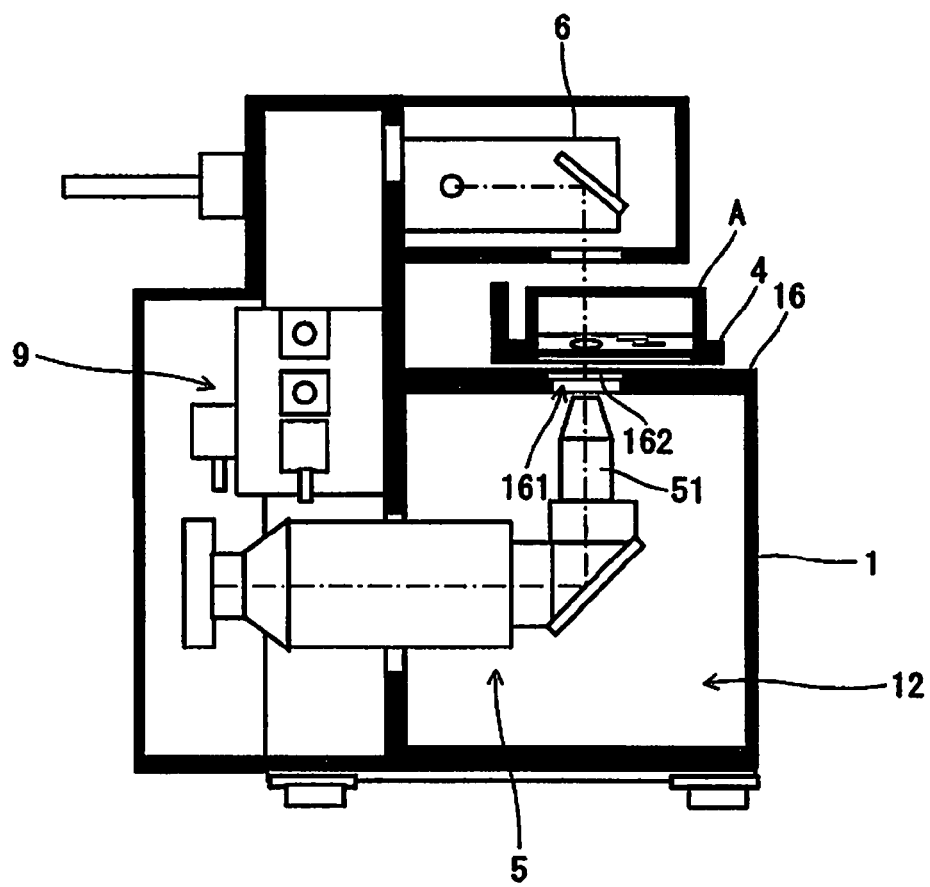
FIG. 24 is a cross-sectional view of an observation unit according to a fifth modification.

FIG. 24 is a cross-sectional view of an observation unit according to a fifth modification. As shown in FIG. 24, the observation unit can have a configuration without the heat insulating member 8 or the case 81 shown in FIG. 6. In particular, the top surface wall 16 of the casing 1 forming the top part of the second space 12 is arranged above the objective lens 51 of the observation device 5, and a light transmission plate 162 is fitted in the through-hole 161 defined in the top surface wall 16 with no space therebetween. The placing table 4 is placed immediately above the top surface wall 16 of the casing 1 while being separated from the top surface wall 16.

The observation unit according to this fifth modification also can be used in the storage 101 and can inhibit heat transfer from the heat source to the sample.

Of course, even in the case where the observation unit shown in FIG. 6 has the configuration without the heat insulating member 8 or the case 81, the tubular member 151 can remain so that the placing table 4 is arranged on a top surface side of the tubular member 151.

The present invention is not limited to the foregoing embodiments in construction but can be modified variously within the technical range set forth in the appended claims.

It is also possible to apply the configuration of sealing the inside space by the casing 1, the configuration of preventing heat transfer by the shielding member 7, the configuration of providing the heat insulating member 8, and the like described above to the observation unit without a mechanism of moving the placing table 4, i.e. the observation unit without the X-axis motor 91 and the X-axis drive mechanism 2, or the Y-axis motor 92 and the Y-axis drive mechanism 3.

What is claimed is:

1. An observation unit comprising:
    an observation device observing a sample,
    a placing table on which the sample is placed,
    a drive device moving the placing table to an observation position where the sample is observed by the observation device, and
    a casing sealing a first space extending in a vertical direction, wherein
    the first space and a second space are defined in the casing,
    the first space is located on the rear surface side of the casing,
    the second space and the placing table are located on the front surface side of the casing,
    the drive device is arranged in the first space,
    the observation device comprises an optical system and an imaging system,
    the imaging system is arranged in the first space while the optical system is arranged in the second space arranged below the placing table and sealed by the casing,
    a shielding member preventing heat transfer from the first space to the placing table and the second space, is interposed between the first space and the placing table, and between the first space and the second space, and
    a light transmission part transmitting light from the observation position downward to the optical system of the observation device is formed on an upper surface wall of the casing, the upper surface wall forming a to part of the second space.

2. The observation unit according to claim 1, wherein
    a heat insulating layer is formed between the top surface wall of the casing forming the top part of the second space and the placing table.

3. The observation unit according to claim 2, wherein
    at least a part of the heat insulating layer is formed by a heat insulating member, and
    the light transmission part penetrates the heat insulating member to be exposed on a surface of the heat insulating member.

4. The observation unit according to claim 1, wherein
    the placing table is capable of reciprocating between the observation position and a separated position which is separated from a position above the second space, and
    reciprocating movement of the placing table is executed by the drive device.

5. The observation unit according to claim 1, wherein
    drive force of the drive device is transmitted to the placing table by a transmission member,
    the placing table can be attached to and detached from the transmission member,
    the transmission member is provided with a detection part while the placing table is provided with a to-be-detected part which is to be detected by the detection part, and
    the to-be-detected part is arranged so that a center of the sample placed on the placing table matches a predetermined position when the to-be-detected part is detected by the detection part.

\* \* \* \* \*